US011532132B2

(12) United States Patent
Musara

(10) Patent No.: US 11,532,132 B2
(45) Date of Patent: Dec. 20, 2022

(54) ADAPTIVE INTERACTIVE MEDICAL TRAINING PROGRAM WITH VIRTUAL PATIENTS

(71) Applicant: Mubayiwa Cornelious Musara, Fulton, MD (US)

(72) Inventor: Mubayiwa Cornelious Musara, Fulton, MD (US)

(*) Notice: Subject to any disclaimer, the term of this patent is extended or adjusted under 35 U.S.C. 154(b) by 0 days.

(21) Appl. No.: 16/811,364

(22) Filed: Mar. 6, 2020

(65) Prior Publication Data

US 2020/0286294 A1 Sep. 10, 2020

Related U.S. Application Data

(60) Provisional application No. 62/815,524, filed on Mar. 8, 2019.

(51) Int. Cl.
*G06T 19/00* (2011.01)
*G06N 20/00* (2019.01)
(Continued)

(52) U.S. Cl.
CPC ........... *G06T 19/006* (2013.01); *G06N 20/00* (2019.01); *G16H 10/60* (2018.01); *G16H 50/20* (2018.01);
(Continued)

(58) Field of Classification Search
CPC ........ G16H 50/50; G16H 10/60; G16H 50/30; G16H 50/20; G16H 80/00; G16H 70/20;
(Continued)

(56) References Cited

U.S. PATENT DOCUMENTS 5,385,474 A * 1/1995 Brindle .................. G09B 23/28
434/262
5,481,649 A * 1/1996 Birdwell .............. G05B 13/028
700/49

(Continued)

FOREIGN PATENT DOCUMENTS

WO 2007059477 A2 5/2007
WO 2019209195 A1 10/2019

OTHER PUBLICATIONS

Alex Chen M.D. et al., "Intraoperative 125I brachytherapy for high-risk stage I non-small cell lung carcinoma", International Journal of Radiation Oncology*Biology*Physics, vol. 44, Issue 5, Jul. 15, 1999, 1 page (Abstract only).

(Continued)

*Primary Examiner* — Charles L Beard
(74) *Attorney, Agent, or Firm* — Edell, Shapiro & Finnan, LLC

(57) ABSTRACT

Methods, systems and computer program products are provided for simulating medical management of a virtual patient. In aspects, a computer model is configured to simulate a medical state of a virtual patient, wherein the model comprises a plurality of decision-based pathways, and wherein the virtual patient is associated with a medical condition of a medical subject category. Input is received from a user of a client device, wherein the input is applied to the model to cause progression along nodes of a decision-based pathway, wherein progression along the decision-based pathway corresponds to a change in a medical state of the virtual patient. When the received input causes progression along a decision-based pathway that is not in accordance with accepted medical standards, progression of a catastrophic sequence of the model for the virtual patient is initiated. The decision-based pathway may be traversed (Continued)

based on input from the user, wherein components of the decision-based pathway correspond to changes in a medical state of the virtual patient.

20 Claims, 5 Drawing Sheets

(51) Int. Cl.
*G16H 50/20* (2018.01)
*G16H 10/60* (2018.01)
*G16H 80/00* (2018.01)
*G16H 50/50* (2018.01)
*G16H 50/30* (2018.01)

(52) U.S. Cl.
CPC ............. *G16H 50/30* (2018.01); *G16H 50/50* (2018.01); *G16H 80/00* (2018.01); *G06T 2210/41* (2013.01)

(58) Field of Classification Search
CPC ... G06N 20/00; G06T 19/006; G06T 2210/41; G06T 13/40; G06F 3/011; G09B 23/28; G09B 9/00; A61B 34/10; A61B 34/25; A61B 2034/101
See application file for complete search history.

(56) References Cited

U.S. PATENT DOCUMENTS

| | | | | |
|---|---|---|---|---|
| 5,634,087 | A * | 5/1997 | Mammone | G06N 3/063 706/25 |
| 5,799,311 | A * | 8/1998 | Agrawal | G06F 16/35 |
| 5,853,292 | A * | 12/1998 | Eggert | G09B 23/28 434/262 |
| 5,870,735 | A * | 2/1999 | Agrawal | G06F 16/35 |
| 5,878,261 | A * | 3/1999 | Holler | G06F 9/4484 717/157 |
| 6,230,151 | B1 * | 5/2001 | Agrawal | G06N 5/003 706/12 |
| 6,247,016 | B1 * | 6/2001 | Rastogi | G06K 9/6282 |
| 6,334,192 | B1 * | 12/2001 | Karpf | G16H 50/30 714/1 |
| 6,519,580 | B1 * | 2/2003 | Johnson | G06K 9/6282 706/47 |
| 6,692,258 | B1 * | 2/2004 | Kurzweil | G09B 23/28 434/262 |
| 6,747,672 | B1 * | 6/2004 | Haakonsen | G16H 50/50 715/764 |
| 7,024,399 | B2 * | 4/2006 | Sumner, II | G16H 50/50 706/45 |
| 7,107,253 | B1 | 9/2006 | Sumner et al. | |
| 7,114,954 | B2 * | 10/2006 | Eggert | G09B 23/30 434/262 |
| 7,277,874 | B2 | 10/2007 | Sumner, II et al. | |
| 7,386,432 | B1 * | 6/2008 | Haakonsen | H04L 67/34 434/262 |
| 7,811,090 | B2 * | 10/2010 | Eggert | G09B 23/28 434/273 |
| 7,925,605 | B1 * | 4/2011 | Rubin | G06N 5/025 706/47 |
| 7,937,336 | B1 * | 5/2011 | Maynard-Zhang | H04L 67/18 706/12 |
| 8,096,811 | B2 * | 1/2012 | Sumner, II | G09B 7/02 434/262 |
| 8,382,485 | B2 * | 2/2013 | Bardsley | G09B 23/32 434/262 |
| 8,393,905 | B2 * | 3/2013 | Kozmenko | G09B 7/00 434/262 |
| 8,469,713 | B2 * | 6/2013 | Kron | G09B 5/065 434/238 |
| 8,647,124 | B2 | 2/2014 | Bardsley et al. | |
| 8,923,631 | B2 * | 12/2014 | Spencer | A61B 8/5223 382/226 |
| 8,961,188 | B1 * | 2/2015 | Singh | G16H 10/60 434/262 |
| 9,104,791 | B2 * | 8/2015 | Cohen | G09B 23/30 |
| 9,177,247 | B2 * | 11/2015 | Stergiou | H04L 67/12 |
| 9,858,540 | B2 * | 1/2018 | Firminger | G06Q 30/06 |
| 9,886,873 | B2 * | 2/2018 | Patrickson | G09B 23/30 |
| 9,892,564 | B1 * | 2/2018 | Cvetko | A61B 5/0071 |
| 10,229,287 | B2 * | 3/2019 | Nerurkar | G06F 16/25 |
| 10,398,389 | B1 * | 9/2019 | D'Alessandro | A61B 5/14532 |
| 10,425,257 | B1 * | 9/2019 | Shakiba | H04L 25/03267 |
| 10,438,497 | B2 * | 10/2019 | Patrickson | G06Q 30/018 |
| 10,541,054 | B2 * | 1/2020 | Zalis | G16H 70/20 |
| 10,665,343 | B1 * | 5/2020 | Davenport | G06N 5/045 |
| 10,828,107 | B2 * | 11/2020 | Sela | G09B 23/285 |
| 10,838,210 | B2 * | 11/2020 | Robaina | G02B 27/01 |
| 10,886,015 | B2 * | 1/2021 | Wolf | A61B 34/70 |
| 11,061,674 | B2 * | 7/2021 | Edvenson | G06F 9/30109 |
| 11,342,051 | B1 * | 5/2022 | Jain | H04W 4/80 |
| 2003/0233641 | A1 * | 12/2003 | Hank | G06F 8/433 717/156 |
| 2004/0044295 | A1 * | 3/2004 | Reinert | A61B 34/20 600/587 |
| 2004/0064298 | A1 * | 4/2004 | Levine | G09B 23/28 703/11 |
| 2004/0181553 | A1 * | 9/2004 | Stockfisch | G06N 5/022 |
| 2004/0225631 | A1 * | 11/2004 | Elnaffar | G06N 20/00 |
| 2005/0170323 | A1 * | 8/2005 | Jarrell | G09B 23/28 434/262 |
| 2005/0177399 | A1 * | 8/2005 | Park | G06Q 10/10 705/3 |
| 2005/0246307 | A1 * | 11/2005 | Bala | G06N 7/005 706/52 |
| 2006/0287861 | A1 * | 12/2006 | Fischer | G10L 13/06 704/260 |
| 2007/0027972 | A1 * | 2/2007 | Agrawal | H04L 67/34 709/223 |
| 2007/0175720 | A1 * | 8/2007 | Yoshida | F16H 57/0434 192/3.63 |
| 2008/0015418 | A1 * | 1/2008 | Jarrell | G16H 70/20 600/300 |
| 2008/0031413 | A1 * | 2/2008 | Bouvier | A61B 6/545 378/63 |
| 2009/0119282 | A1 * | 5/2009 | Load | G16H 70/60 707/999.005 |
| 2009/0150134 | A1 * | 6/2009 | De Leon | G16H 40/20 703/11 |
| 2009/0185731 | A1 * | 7/2009 | Ray | G06T 7/12 382/131 |
| 2009/0215011 | A1 * | 8/2009 | Christensen | G09B 23/28 434/29 |
| 2009/0281841 | A1 * | 11/2009 | Basak | G06Q 40/08 705/4 |
| 2010/0092936 | A1 * | 4/2010 | Pfingsten | G09B 23/28 434/262 |
| 2010/0217744 | A1 * | 8/2010 | Demirdjian | G06N 20/00 706/58 |
| 2010/0305919 | A1 * | 12/2010 | Gan | G06F 11/3608 703/2 |
| 2010/0311028 | A1 * | 12/2010 | Bell, III | G09B 9/00 434/263 |
| 2011/0002513 | A1 * | 1/2011 | Molinari | G16H 30/20 382/128 |
| 2011/0046978 | A1 * | 2/2011 | Gordon | G06Q 99/00 705/2 |
| 2011/0159470 | A1 * | 6/2011 | Hradek | G09B 23/28 434/262 |
| 2011/0165542 | A1 * | 7/2011 | Campbell | G09B 7/00 434/219 |
| 2012/0004894 | A1 * | 1/2012 | Butler | G16H 10/60 703/11 |
| 2012/0064497 | A1 * | 3/2012 | Wu | G09B 23/288 434/265 |
| 2012/0259807 | A1 * | 10/2012 | Dymetman | G06F 17/18 706/50 |

(56) References Cited

U.S. PATENT DOCUMENTS

| | | | | |
|---|---|---|---|---|
| 2012/0280988 | A1* | 11/2012 | Lampotang | G06T 19/006 345/419 |
| 2012/0310667 | A1* | 12/2012 | Altman | G16H 50/20 705/3 |
| 2013/0044924 | A1* | 2/2013 | Spencer | A61B 8/5223 382/128 |
| 2013/0151444 | A1* | 6/2013 | Blaschko | G06N 20/00 706/12 |
| 2013/0308694 | A1* | 11/2013 | Amamiya | H04L 25/03057 375/233 |
| 2014/0099617 | A1* | 4/2014 | Tallman, Jr. | G09B 23/288 434/262 |
| 2014/0127662 | A1 | 5/2014 | Kron et al. | |
| 2014/0287395 | A1* | 9/2014 | Silverglate | G09B 23/28 434/266 |
| 2014/0337269 | A1* | 11/2014 | Eads | G06N 5/02 706/46 |
| 2014/0370468 | A1 | 12/2014 | Kron et al. | |
| 2014/0370475 | A1* | 12/2014 | Bova | G09B 23/285 434/267 |
| 2015/0005785 | A1* | 1/2015 | Olson | A61B 34/30 606/130 |
| 2015/0100290 | A1* | 4/2015 | Falt | A61N 5/1075 703/2 |
| 2015/0106111 | A1* | 4/2015 | Gray | G06F 16/9535 705/2 |
| 2015/0155971 | A1* | 6/2015 | Dvoretzki | H04L 25/03242 375/347 |
| 2015/0227701 | A1* | 8/2015 | Nicolaas | G16H 50/20 705/2 |
| 2015/0335304 | A1* | 11/2015 | Lavi | A61B 5/02007 600/407 |
| 2015/0339847 | A1* | 11/2015 | Benishti | A61M 5/007 382/131 |
| 2015/0342551 | A1* | 12/2015 | Lavi | A61B 6/5235 600/431 |
| 2015/0371141 | A1* | 12/2015 | Yeon | G06N 20/00 706/12 |
| 2016/0012349 | A1* | 1/2016 | Lai | G16H 50/20 706/12 |
| 2016/0104312 | A1* | 4/2016 | Zino | G06V 10/40 345/427 |
| 2016/0191887 | A1* | 6/2016 | Casas | G06F 3/011 348/47 |
| 2016/0252363 | A1* | 9/2016 | Tertoolen | G06V 20/588 701/410 |
| 2016/0253473 | A1* | 9/2016 | Anderson | G16H 50/70 705/2 |
| 2017/0026515 | A1* | 1/2017 | Bernstein | G06Q 10/02 |
| 2017/0071673 | A1* | 3/2017 | Ferro | A61B 5/0077 |
| 2017/0076208 | A1* | 3/2017 | Huang | G06F 16/9535 |
| 2017/0140114 | A1* | 5/2017 | Are | G16H 50/20 |
| 2017/0161370 | A1* | 6/2017 | Endo | G06F 16/3344 |
| 2017/0188976 | A1* | 7/2017 | Kalra | G16H 10/20 |
| 2017/0213473 | A1* | 7/2017 | Ribeira | G09B 5/10 |
| 2017/0220927 | A1* | 8/2017 | Takigawa | B23K 26/21 |
| 2017/0312032 | A1* | 11/2017 | Amanatullah | G09B 23/30 |
| 2018/0090029 | A1* | 3/2018 | Fisher | G09B 23/28 |
| 2018/0098813 | A1* | 4/2018 | Nesichi | A61B 34/10 |
| 2018/0120947 | A1* | 5/2018 | Wells | G06F 3/017 |
| 2018/0168780 | A1* | 6/2018 | Kopelman | A61B 34/10 |
| 2018/0200018 | A1* | 7/2018 | Silva | G06F 3/017 |
| 2018/0260531 | A1* | 9/2018 | Nori | G06N 20/00 |
| 2018/0260719 | A1* | 9/2018 | Nori | G06N 20/20 |
| 2018/0322941 | A1* | 11/2018 | Krishnan | G16H 40/63 |
| 2018/0338806 | A1* | 11/2018 | Grubbs | A61B 34/10 |
| 2019/0034834 | A1* | 1/2019 | Jiang | G06F 9/4881 |
| 2019/0053855 | A1* | 2/2019 | Siemionow | A61B 34/30 |
| 2019/0057620 | A1* | 2/2019 | Eggert | G09B 5/14 |
| 2019/0060001 | A1* | 2/2019 | Kohli | A61B 90/37 |
| 2019/0108019 | A1* | 4/2019 | Edvenson | G06F 9/3893 |
| 2019/0122139 | A1* | 4/2019 | Perez | G06N 20/00 |
| 2019/0122162 | A1* | 4/2019 | Abhinav | G06Q 50/01 |
| 2019/0130644 | A1* | 5/2019 | Mate | G06T 19/006 |
| 2019/0180637 | A1* | 6/2019 | Mealer | G09B 23/28 |
| 2019/0201136 | A1* | 7/2019 | Shelton, IV | A61B 90/53 |
| 2019/0206562 | A1* | 7/2019 | Shelton, IV | B25J 13/006 |
| 2019/0214126 | A1* | 7/2019 | Goetz | G06T 19/00 |
| 2019/0236415 | A1* | 8/2019 | Pyko | G06K 9/6282 |
| 2019/0293443 | A1* | 9/2019 | Kelly | G01C 21/3492 |
| 2019/0339525 | A1* | 11/2019 | Yanof | A61B 34/20 |
| 2019/0340956 | A1* | 11/2019 | Lindkvist | G09B 23/30 |
| 2019/0348169 | A1* | 11/2019 | Gibby | G06K 7/1417 |
| 2019/0355124 | A1* | 11/2019 | Zhou | G06N 5/003 |
| 2019/0362651 | A1* | 11/2019 | Barral | G06N 3/08 |
| 2019/0380792 | A1* | 12/2019 | Poltaretskyi | A61B 34/25 |
| 2019/0388732 | A1* | 12/2019 | Pichiliani | A63B 24/0062 |
| 2019/0392332 | A1* | 12/2019 | Choi | G06F 16/2246 |
| 2020/0008772 | A1* | 1/2020 | Ghamari | G09B 23/286 |
| 2020/0020171 | A1* | 1/2020 | Hendricks | G06T 19/006 |
| 2020/0030044 | A1* | 1/2020 | Wang | G16H 50/50 |
| 2020/0035359 | A1* | 1/2020 | Erpenbach | G16H 20/00 |
| 2020/0037943 | A1* | 2/2020 | Chaja | G06F 9/542 |
| 2020/0050954 | A1* | 2/2020 | Fukushima | G06N 20/00 |
| 2020/0050963 | A1* | 2/2020 | Tanaka | G06K 9/6282 |
| 2020/0051694 | A1* | 2/2020 | Goldberg | G16H 50/20 |
| 2020/0065395 | A1* | 2/2020 | Pereira | G06F 16/24578 |
| 2020/0065707 | A1* | 2/2020 | Kasahara | G06N 5/003 |
| 2020/0066391 | A1* | 2/2020 | Sachdeva | A61C 5/30 |
| 2020/0074331 | A1* | 3/2020 | Arendt | G06K 9/6276 |
| 2020/0081523 | A1* | 3/2020 | Liu | G06T 3/40 |
| 2020/0081934 | A1* | 3/2020 | Karwan | G06F 16/958 |
| 2020/0090076 | A1* | 3/2020 | Katoh | G06N 5/003 |
| 2020/0111376 | A1* | 4/2020 | Breeding | G06T 11/00 |
| 2020/0117523 | A1* | 4/2020 | Morrison | G06N 20/20 |
| 2020/0118691 | A1* | 4/2020 | Kiljanek | G06N 20/20 |
| 2020/0125236 | A1* | 4/2020 | Palushi | A61B 90/37 |
| 2020/0143284 | A1* | 5/2020 | Tanaka | G06N 20/00 |
| 2020/0143285 | A1* | 5/2020 | Tanaka | G06N 20/00 |
| 2020/0159313 | A1* | 5/2020 | Gibby | G06T 19/006 |
| 2020/0174437 | A1* | 6/2020 | Hu | G06N 5/003 |
| 2020/0188028 | A1* | 6/2020 | Feiner | G16H 50/50 |
| 2020/0211696 | A1* | 7/2020 | Weaver | G06T 11/00 |
| 2020/0258639 | A1* | 8/2020 | Tschulena | G16H 50/50 |
| 2020/0273373 | A1* | 8/2020 | Grant | G16H 50/50 |
| 2020/0281657 | A1* | 9/2020 | Moyer | A61B 90/36 |
| 2020/0293907 | A1* | 9/2020 | Kasahara | G06N 5/003 |
| 2020/0311142 | A1* | 10/2020 | Edelman | G06F 16/27 |
| 2020/0333428 | A1* | 10/2020 | Sun | G01S 5/16 |
| 2020/0334998 | A1* | 10/2020 | Sun | G06F 3/147 |
| 2020/0335206 | A1* | 10/2020 | Yamagata | G16H 20/00 |
| 2020/0350063 | A1* | 11/2020 | Thornton | G06K 9/00691 |
| 2020/0352652 | A1* | 11/2020 | Amit | G16H 50/50 |
| 2020/0357176 | A1* | 11/2020 | Crowther | G06F 3/016 |
| 2020/0357299 | A1* | 11/2020 | Patel | G06F 3/011 |
| 2020/0357513 | A1* | 11/2020 | Katra | G16H 15/00 |
| 2020/0365273 | A1* | 11/2020 | Mitsumori | G16H 50/20 |
| 2020/0372400 | A1* | 11/2020 | Carreira-Perpin | G06F 16/9027 |
| 2020/0388397 | A1* | 12/2020 | Shoaran | G16H 50/20 |
| 2021/0012240 | A1* | 1/2021 | Tanaka | G06N 20/20 |
| 2021/0019047 | A1* | 1/2021 | Zhang | G06F 3/061 |
| 2021/0055357 | A1* | 2/2021 | Yeh | G01R 31/58 |
| 2021/0065007 | A1* | 3/2021 | Interlandi | G06N 3/0454 |
| 2021/0090451 | A1* | 3/2021 | Frist, Jr. | G09B 23/288 |
| 2021/0093391 | A1* | 4/2021 | Poltaretskyi | A61B 5/1114 |
| 2021/0109819 | A1* | 4/2021 | Liu | G06F 16/24568 |
| 2021/0125101 | A1* | 4/2021 | Idesawa | G06N 20/20 |
| 2021/0133017 | A1* | 5/2021 | Cheng | G06F 11/0778 |
| 2021/0133515 | A1* | 5/2021 | Biswas | G06N 20/00 |
| 2021/0134418 | A1* | 5/2021 | Frieder | G16H 70/40 |
| 2021/0149918 | A1* | 5/2021 | Finkler | G06N 20/00 |
| 2021/0158224 | A1* | 5/2021 | Tanaka | G06N 20/20 |
| 2021/0165481 | A1* | 6/2021 | Brugarolas Brufau | A63F 13/60 |
| 2021/0174223 | A1* | 6/2021 | Dodwell | G06N 5/04 |
| 2021/0174954 | A1* | 6/2021 | Truschel | A61B 5/0008 |
| 2021/0200896 | A1* | 7/2021 | Lilja | G06N 20/00 |
| 2021/0201187 | A1* | 7/2021 | Olivadese | G06N 10/00 |
| 2021/0240174 | A1* | 8/2021 | Wang | G05B 23/0281 |
| 2021/0248922 | A1* | 8/2021 | Gordon | G09B 9/00 |
| 2021/0312833 | A1* | 10/2021 | Betteridge | G16H 50/20 |

(56) References Cited

U.S. PATENT DOCUMENTS

| | | | | |
|---|---|---|---|---|
| 2021/0343427 | A1* | 11/2021 | Frist, Jr. | G16H 50/20 |
| 2022/0005369 | A1* | 1/2022 | Frist, Jr. | G09B 23/288 |
| 2022/0084633 | A1* | 3/2022 | Das | G16H 50/20 |
| 2022/0084662 | A1* | 3/2022 | Das | A61B 5/02055 |
| 2022/0093008 | A1* | 3/2022 | Nicolosi | G09B 23/285 |
| 2022/0093241 | A1* | 3/2022 | Scanlin | G16H 40/63 |
| 2022/0115125 | A1* | 4/2022 | Yamakawa | G16H 50/30 |
| 2022/0115131 | A1* | 4/2022 | Baronov | G16H 10/60 |
| 2022/0115132 | A1* | 4/2022 | Baronov | G16H 50/20 |
| 2022/0192596 | A1* | 6/2022 | Fathieh | G16H 50/20 |
| 2022/0215961 | A1* | 7/2022 | Jacobs | G16H 40/67 |
| 2022/0230759 | A1* | 7/2022 | Abu El Ata | G16H 15/00 |

OTHER PUBLICATIONS

Hiran C. Fernando et al., "Impact of Brachytherapy on Local recurrence rates after sublobar resection: Results from ACOSOG Z4032 (Alliance) A Phase III Randomized trial for high risk operable non-small cell Lung cancer", Journal of Clinical Oncology: vol. 32, Issue 23, Aug. 10, 2014, 10 pages.

George Voynov et al., "Intraoperative 125I Vicryl mesh brachytherapy after sublobar resection for high-risk stage I nonsmall cell lung cancer", Brachytherapy: vol. 4, Issue 4, Mar. 2005, 8 pages.

Karen Lynne Leonard et al., "A novel ytterbium-169 brachytherapy source and delivery system for use in conjunction with minimally invasive wedge resection of early stage lung cancer", Brachytherapy, Mar.-Apr. 2011, 10(2), 14 pages.

PCT International Search Report and the Written Opinion, PCT/US2020/21382, dated Apr. 26, 2020, 26 pages.

\* cited by examiner

ADAPTIVE INTERACTIVE MEDICAL TRAINING PROGRAM WITH VIRTUAL PATIENTS

CROSS-REFERENCE TO RELATED APPLICATIONS

This application claims priority to U.S. Provisional Application No. 62/815,524, filed Mar. 8, 2019, the contents of which are hereby incorporated by reference in their entirety.

FIELD OF THE INVENTION

Present invention embodiments relate to virtual medical training programs, and in particular, to adaptive and dynamic interactive medical training programs or simulators using virtual patients.

BACKGROUND

Medical technology has dramatically advanced over the past several decades. With advances in surgical techniques, available medicines, and diagnostics, physicians have access to a wide range of technologies to diagnose and treat patients. In critical care settings, such as hospitals and in particular emergency rooms, physicians need to be able to quickly and effectively assess the severity of a medical condition of a patient, and to respond by ordering appropriate diagnostic testing and by selecting and implementing an appropriate management plan.

Traditional methods of medical training have involved shadowing a physician or hands on experience under the supervision of a senior resident or attending physician. Both of these approaches have limitations. For example, a medical student who is shadowing a physician may not gain the necessary and essential hands on experience. On the other hand, junior physicians under the supervision of senior physicians may not gain sufficient experience and exposure in managing complex medical cases, as the senior physician may intercede early to prevent incorrect medical management protocols or to manage cases deemed too complex for the junior level. Yet in some rotations the student or junior may not be exposed to such cases. Thus, both of these approaches may limit training opportunities for students and junior practitioners.

Even with access to a wide range of medical diagnostics and treatments, it is challenging for medical practitioners to manage complex cases, especially when having no previous exposure or experience with such complex cases and this may lead to medical errors or oversight, which may lead to an adverse outcome.

SUMMARY

According to the techniques disclosed herein, methods, systems, and computer program products are provided to simulate assessment, diagnosis and management of a virtual patient, wherein the virtual patient presents with complex, interrelated, and dynamic medical conditions.

A computer model configured to simulate (e.g., a simulator) a medical condition of a virtual patient is generated or obtained, wherein the model comprises a plurality of decision-based pathways comprising a series of nodes, and wherein the virtual patient is associated with a medical condition of a medical specialty subject category. Input is received from a user of a client device, wherein the input is applied to the model resulting in progression along nodes of a decision-based pathway, wherein progression along the decision-based pathway corresponds to a change in the medical state of the virtual patient. When the received input causes deviation from an accepted medical management plan/standard of care, progression to a catastrophic sequence of events in the virtual patient model may be initiated, while allowing the user to continue to provide inputs to progress along nodes of the decision-based pathway.

In other aspects, a deviation from an accepted medical management plan causes downstream complications or demise of the virtual patient.

In aspects, a decision-based pathway is traversed once during simulation of the model.

In other aspects, the first decision pathway and the second decision pathway are different based on variations in user decisions but may comprise overlapping nodes.

In aspects, the user discovers the medical deviation and reverses the catastrophic sequence.

In other aspects, the medical simulator engine tracks nodes that have been previously traversed in order to prevent a pathway from being displayed more than once during a simulation by varying complexity and acuity of the medical condition.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. The invention may take form in various components and arrangements of components, and in various steps and arrangements of steps. The drawings are only for purposes of illustrating preferred embodiments and are not to be construed as limiting the invention. The accompanying drawings, which are incorporated herein and form part of the specification, illustrate various embodiments of the present invention and, together with the description, further serve to explain the principles of various embodiments of the invention and to enable a person skilled in the pertinent art to make and use the various embodiments of the invention. In the drawings, like reference numbers indicate identical or functionally similar elements.

DETAILED DESCRIPTION

Methods, systems, and computer program products are provided for simulating simple to complex, interrelated, and dynamic medical conditions using virtual patient models. An interactive virtual patient simulator is provided to simulate complex medical diseases to improve medical training for medical students, physicians, and auxiliary medical personnel. In particular, the virtual patient simulator simulates complex medical cases for which comprehensive and advanced clinical medical knowledge is needed, in order to improve training of medical personnel and professionals. The system may be used for all medical practitioners including but not limited to EMT/EMS personnel, nurses, physician assistants, medical students, residents, junior and mid-level medical practitioners, as well as senior practicing clinicians.

Figure 1:
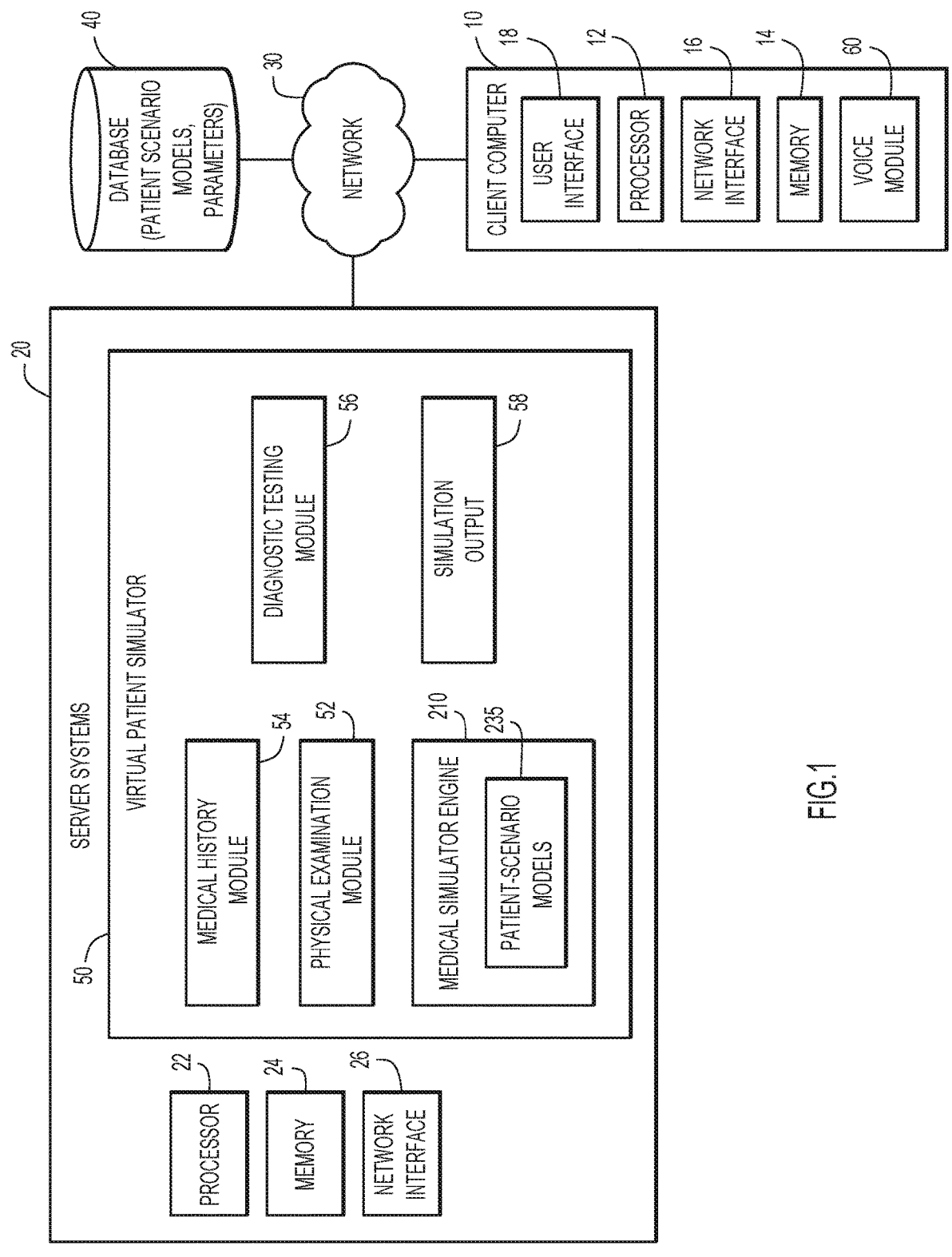
FIG. 1 is a block diagram illustrating an example of a computing environment of a virtual patient simulation system, according to embodiments provided herein.

With reference now to FIG. 1, a block diagram is shown of an example of a computing environment 100 in which aspects of the embodiments provided herein may be implemented. The computing environment 100 may include at least one end-user or client computer 10 and at least one server system 20. Client computer 10 and server system 20 may communicate over a network 30. Server system 20 may also communicate with databases 40, which may store patient-scenario models for users of the system. Each user of the system may make decisions, provided in the form of inputs to the virtual patient simulator 50, which determine the progression of a medical condition of the virtual patient and which portions of patient-scenario models are presented to the user during subsequent simulations. Accordingly, database 40 may contain information, specific to each user of the system, relating to historical interactions (inputs) with the simulator and to portions of patient-scenario models displayed to the user. This approach provides a methodology to vary the content of a medical subject category that is presented to the user so that the user cannot rely upon memorized answers to pass the simulation. Thus, the system presents different portions of patient-scenario models to the user when repeating the scenario after each unsuccessful attempt of a simulation allowing an interactive and dynamic approach that adapts the output of the simulator to the user, based on prior and new inputs from the user.

Although a single database is shown, it is understood that the server may communicate with any number of databases or other sources of data having medical information, which may be used for the simulation of a virtual patient. In an example embodiment, server system 20 may be configured to communicate with one or more servers comprising medical history information, physical examination information, diagnostic testing information, and/or a case vignette (e.g., a short summary).

In the example embodiment shown in FIG. 1, server system 20 includes one or more processors 22 (e.g., a CPU, a GPU, a microprocessor, a microcontroller, a controller, etc.), a memory 24 (e.g., RAM, ROM, EPROM, flash, etc.), a network interface 26 (e.g., modem, network card, etc.), and a virtual patient simulator 50. The computer readable program for the virtual patient simulator 50 may be stored in memory 24 or some other non-transitory computer readable medium. In this embodiment, virtual patient simulator 50 is shown relative to a single server system 20. However, it is understood that the virtual patient simulator may be distributed across a plurality of servers or other computing devices.

Virtual patient simulator 50 may comprise medical history module 54, diagnostic testing module 56, physical examination module 52, medical simulator engine 210, and simulation output 58. In some embodiments, at the beginning of a simulation, the virtual patient simulator may provide a case vignette 105 (see, e.g., FIG. 2) to the user, which includes a brief summary of the medical state of the virtual patient (e.g., symptoms, initial medical presentation, etc.). With this information, the user interacts with the virtual patient simulator 50, including medical history module 54, physical examination module 52, and diagnostic testing module 56 to obtain additional information regarding the virtual patient. Once the additional information is obtained, this information is utilized during the virtual patient simulation.

Medical history module 54 allows a user to dynamically interact with the module to obtain additional information (see, FIG. 2 medical history information 110) about the medical history of the virtual patient. The medical history may include preexisting medical conditions, family history, present medical conditions, current medications, past surgical history, allergies to medications, social history and habits, genetic history, etc. In some aspects, the user may interact with module 54, for example, presenting questions to the module regarding one or more of the above categories, to obtain additional information about the medical history of the patient. In some cases, the medical history of the patient may contain information, which if not ascertained by the user, may trigger a catastrophic event at a subsequent later point in the simulation pathway as the absent information would be vital for management of the virtual patient. For example, if the user fails to ascertain whether a patient is allergic to drugs or other medications, the virtual patient simulator may simulate an allergic reaction during the simulation. For example, the user may select administration of a particular drug to which the patient has an allergy, and this may trigger a catastrophic event that may lead to the demise of the virtual patient. In other cases, the virtual patient system comprising patient scenario models may simulate a reaction that leads to the demise of the virtual patient, independently of administration of a specific drug. In this case, the reaction may be triggered by failure to obtain a complete medical history such as the patient taking anticoagulation medications resulting in uncontrolled bleeding. In general, any suitable type of medical history information that the user failed to obtain may be utilized to trigger a catastrophic event at some future point in the pathway.

Physical examination module 52 allows the user to dynamically interact with this module to obtain additional information (see, FIG. 2 physical examination information 115) about the physical state of the virtual patient. This may include the general state of the virtual patient, appearance, current state of the patient, evolving symptoms, vitals, signs, physical exam findings, etc. In some aspects, the user may interact with the physical examination module 54, for example, presenting questions to the module regarding one or more of the above categories to obtain additional information about the physical state of the patient. In some cases, if the user fails to obtain critical information during interaction with the physical examination module, the virtual patient simulator may trigger a catastrophic event during the simulation.

In an embodiment, the user may interact with the simulator to conduct a virtual physical examination, in order to gather additional physical examination information. For example, if the user fails to virtually perform or identify an aspect of a physical exam, such as testing a patient with lower right abdominal pain for rebound tenderness (a clinical sign known as McBurney's Point tenderness that is associated with appendicitis), a related catastrophic event (e.g., perforation of appendix) may be triggered during the simulation, which may lead to the demise of the virtual patient during the simulation.

Thus, the user should obtain a complete (or nearly complete) medical history and perform a complete (or nearly complete) physical examination of the virtual patient by asking appropriate series of questions to the simulator. Based on the medical history and/or physical examination information, the user may order specific diagnostic testing, including radiological and laboratory data to reach the appropriate diagnosis.

Diagnostic testing module 56 allows the user to dynamically interact with the module to obtain additional information (see, FIG. 2 diagnostic information 120) about the physiological and anatomic state of the virtual patient. This may include laboratory testing (e.g., bloodwork, tissue analysis, histology, cytology, urine analysis, stool analysis, etc.), radiology (including ultrasounds, MRIs, Echocardiograms, CT scans, etc.). In some aspects, the user may interact with the diagnostic testing module 56, for example, by requesting specific diagnostic tests in order to make a diagnosis of the virtual patient. In some cases, the diagnostic testing of the patient may contain information, which if not ascertained by the user, may trigger a catastrophic event during the simulation. For example, if the user fails to order a specific diagnostic test (e.g., based on the patient presentation/summary, medical history, physical examination, etc.), the virtual patient simulator may trigger a catastrophic event as a result of the undetected condition that may lead to the demise of the virtual patient. For example, if the user fails to order an EKG for a patient experiencing chest pain, or a repeat EKG, when the initial EKG is normal and the virtual patient has symptoms that strongly correlate with angina, a catastrophic event (e.g., heart attack) may be triggered during the simulation leading to the demise of the virtual patient.

With the diagnostic testing module 56, the user may generate a specific list of laboratory tests to be ordered. These tests may be listed on the client computer display. In some aspects, if the user fails to order appropriate laboratory tests, the user is not able to return to this module to order additional tests. For users that are not well-versed in laboratory testing, omissions of relevant laboratory tests may occur, and the user may initiate an inappropriate management plan for the virtual patient and/or a catastrophic sequence may be triggered by the omission of the laboratory test. This allows the user to rectify areas of knowledge deficits before retaking the simulator models.

In other aspects of the diagnostic testing module, the user may order radiological studies, and if no interpretation is offered, the user must review the results/images to reach a diagnosis. CT scan images of subtle free air in the peritoneum may be presented when the user requests a CT scan of the abdomen. Images of pathological specimens may also be included to assess a user's knowledge of pathological slides and images. For example, an image of a teratoma with different tissue types may be provided in response to a magnetic resonance study to diagnose a patient with abdominal pain. Pathology slides and images may also be provided when the user requests surgical resection.

In other cases, laboratory and radiological studies may be unavailable so that a user's ability to make a correct diagnosis and initiate a correct management plan without diagnostic testing is assessed. In other embodiments, the virtual patient simulator may be configured to decrease unnecessary diagnostic testing by limiting the number and types of tests to minimize interaction time with the diagnostic testing module. The goal is to teach the user efficiency and to minimize the cost of diagnostic testing.

Laboratory results and radiological images may vary with repeat simulations of the patient-scenario model, giving each case unique variability and preventing the user from recognizing the medical topic based on memory. This configuration prevents the user from memorizing each case scenario and relying on memory to successfully complete each topic, as may occur during other types of assessments in which missed questions are presented in the same format when the user retakes that section. When presented in the same format, the user may simply memorize answers to questions, and it may not be clear as to whether the user understands the material or if their learning curve has benefitted from the process. In contrast, with the virtual patient simulator, a user may be presented with different patient-scenarios during simulation of a particular medical subject category.

In some aspects, the diagnostic testing module 56 may return virtual patient images for display on the client computer to provide the user with visual and other clues to assist with formulating a diagnosis. For example, images of blue bloater (Chronic bronchitis) versus pink puffer (Emphysema) patients may be provided, or images of superficial soft tissue infections or extremity deformities resulting from injuries may be provided allowing the user to assess disease process severity and to initiate an appropriate management plan.

Generating an incomplete medical history, failing to order appropriate diagnostic tests, interpreting diagnostic data incorrectly, or omitting aspects of a physical exam may result in an inaccurate diagnosis or conclusion, which may result in an inappropriate management plan, and may cause a catastrophic sequence that leads to an undesirable outcome.

Medical simulator engine 210 may comprise patient-scenario models for simulating a medical condition and outcome of a virtual patient. The medical simulation engine may also identify patient-scenario models and/or portions thereof that have been previously presented to the user, so as to avoid presenting repetitive or duplicative information to the user. By presenting a patient-scenario model or portions thereof to a user once, the user is unable to memorize answers, and instead, must rely upon medical knowledge. This teaches the user that diseases have numerous and vastly different presentations and knowledge of the fundamentals is integral in patient management.

In some aspects, the medical simulator engine 210 may trigger a catastrophic sequence based upon input from a user, e.g., from an incorrect medical decision or omission. For example, if the user omits obtaining pertinent information during interacting with the medical history module, the diagnostic testing module, or the physical examination module, the medical simulation engine may identify the missing information, and may trigger a catastrophic event related to the omission of this information.

The medical simulator engine 210 may comprise one or more patient-scenario models 235. In some aspects, a patient-scenario model may be assigned to a specific user. Prior to initiation of the simulation, each user may be associated with the same uninitialized patient-scenario model. When a user initiates the simulation, the patient-scenario model is customized to that user based on the input provided by that user. In some cases, a user may take hours and rarely up to a day in a time limited environment to complete the simulation of a medical subject category. Accordingly, the user customized patient-scenario model, for each user and for each medical subject category, as well as any associated parameters may be stored in database 40 for subsequent retrieval if the case scenario has not been completed or the simulation may start from the beginning. Storing of the user customized patient-scenario model ensures that when the user reengages the simulation at the beginning of the scenario, a previously viewed pathway of the patient-scenario model will not be presented to the user in a subsequent simulation. The user may then proceed with the diagnostic pathways and be allowed to perform the same mistakes if the user has not become educated on the subject matter and learned from the previous mistakes. The user may flag different wrong pathways on the decisions paths along the flow chart resulting in catastrophic results. This will continue each time the user takes the subject matter until the user eventually traverses the correct pathway with the appropriate medical management.

Once a catastrophic event is triggered by the medical simulator engine 210, the simulation may cause the virtual patient to progress through a series of deteriorating states prior to demise of the virtual patient. In some cases, once a catastrophic event is triggered, demise of the virtual patient cannot be reversed, regardless of the interactions of the user. In other cases, if the user selects an appropriate series of actions that leads to identification of the medical condition and the user selects appropriate medical management and treatment, the user may exit the catastrophic sequence, but the virtual patient will have an undesirable outcome to highlight the wrong decisions made in the management pathways.

In some cases, the catastrophic sequence may progress immediately leading to a rapid demise of the virtual patient. For example, the catastrophic sequence may progress at a rate that is faster than the user may compensate for, e.g., by interacting with the simulator to obtain additional information, order diagnostics, and/or treat the patient. In other cases, the catastrophic sequence may be delayed by a preset period of time before being initiated or may progress slowly during the simulation. For example, the catastrophic sequence may progress at a rate that allows the user to compensate for the catastrophic sequence, e.g., by interacting with the simulator to obtain additional information, order diagnostics, and/or treat the patient in a manner that addresses the underlying medical condition causing the catastrophic sequence.

Simulation output 58 may present the state of the virtual patient as generated by the virtual patient simulator. In general, the virtual patient simulator will simulate the condition of the virtual patient using a patient-scenario model in which users provide inputs to traverse a pathway of the patient-scenario model. In some cases, a first pathway may correspond to a correct medical assessment and treatment, while another pathway may correspond to an incorrect medical assessment and/or treatment based on a wrong diagnosis/medical decision. The number of pathways may be determined, at least in part, by the complexity of diagnosing the medical condition.

In some cases, simulation output 58 may present the state of the virtual patient after an input from the user, which results in progression of the simulation along a pathway (of a decision tree or flowchart) of the patient-scenario model. Thus, simulation output 58 may provide results to the user, including results of individual simulations (e.g., from a beginning of a simulation to successful treatment or an unfavorable result) as well as overall results of simulation of the medical subject category.

Server system 20 may include any number of computer processors or central processing units (CPUs) or graphical processing units (GPUs), any number of which may include one or more processing cores. In some embodiments, any of the processing cores may be physical or logical. For example, a single core may be used to implement multiple logical cores using symmetric multi-threading. In other embodiments, the virtual patient simulator 50 may utilize virtual machines. In still other aspects, the virtual patient simulator may operate in any suitable environment, including but not limited to Windows, Linux, Unix, MacOS, etc.

Server system 20 may be connected to database 40, which may store various types of information for virtual patient simulations. In some cases, the modules of server system 20, including virtual patient simulator 50 may send simulation results and patient-scenario models to database 40 via network 30. Database 40 may be implemented by any conventional database unit or storage unit, or equivalent, may be local to or remote from the server 20, and may communicate with the server system 20 through any suitable medium (e.g., wire, cable, wireless, LAN, WAN, Internet, Intranet, VPN, etc.). Networks include but are not limited to wired communication links, wireless communication links, fiber optic communication links, etc. In some aspects, the database may store data in any suitable format, including any format compatible with SQL databases or other databases. In general, database 40 may be a relational database or a non-relational database or a hybrid thereof. Database 40 may be attached to the network, e.g., network attached storage, cloud based data storage system, or other remote storage.

Client computer 10 may be a personal computer, a network computer, a tablet, a smartphone, or any other computing device configured to communicate with server system 20, and may be equipped with a display (e.g., a monitor, a touch screen, a LCD screen, or any physical or virtual interface to display content, etc.) for viewing information (e.g., patient state, diagnostic information, medical history information, physical examination information, etc.) as well as keyboards, mice, keypads, touch screens, or voice capture devices etc., for obtaining and analyzing virtual patient information. Client computer 10 may also comprise commercially available software for operation of the computer (e.g., an operating system, updates, drivers, etc.) as well as server/communications software, browser/interface software for accessing data, etc. Client computer 10 includes one or more processors 12 (e.g., a CPU, a GPU, a microprocessor, a microcontroller, a controller, etc.), a memory 14 (e.g., RAM, ROM, EPROM, flash, etc.), a network interface 16 (e.g., network card, serial interface, etc.), a user interface 18, and a voice module 60. User interface 18 may be configured to display the virtual patient simulation output 58, including virtual patient state and outcome, treatment information and diagnosis information, and medical history information. Additionally, user interface 18 may also be configured to communicate with server system 20, to allow the user to obtain information pertaining to the virtual patient. Thus, user interface 18 may be a graphical user interface (e.g., a GUI, a command line prompt, a menu screen, etc.) that a user may use to obtain information, and may provide reports or other information pertaining to the results of the virtual patient simulator to the user. Client computer 10 may be configured to communicate with server system 20 via a web browser (e.g., by accessing a website hosted by a server), via a web browser plug-in, or via an application program running on the client computer. In some embodiments, voice module 60 may be used to translate audio to text, and this information may be provided to virtual patient simulator 50. In some aspects, the interface between the medical simulator engine and the user may be provided using Dragon or a similar application. The voice module 60 may decrease the total amount of time the user has to process each module. Initially, a dictation type interface may be presented, which decreases the amount of time needed for diagnosing and treating the virtual patient, as typing is not needed. The interaction may be displayed on the user interface in an enhanced manner. In other aspects, a reciprocal voice interaction platform may be provided, allowing the virtual patient simulator to answer questions verbally with respect to the user.

Client computer 10 may be connected to server system 20 via any suitable communication network 30 including e.g., the Internet, the Intranet, a wide area network (WAN), a local area network (LAN), a wireless link, hardwire, a VPN or a modem. Client computer 10 and server system 20 may be local to or remote from each other. Networks may include but are not limited to wired communication links, wireless communication links, fiber optic communication links, etc.

In some embodiments, the virtual patient simulator may be configured to operate as a standalone unit on a client computer, such that the client computer 10 has access to database 40 and the virtual patient simulator 50. The standalone unit may perform all of the functions of the virtual patient simulator as provided herein.

The client device 10 allows a user to access server system 20 to provide inputs and receive outputs from the virtual patient simulator. The system may allow individual users to access the virtual patient simulator, concurrently or sequentially, and may store output resulting from each simulation separately, e.g., in database 40. This allows different users to provide different inputs for the system, and for the simulation to store models specific to each person and based on their previous input.

Figure 2:
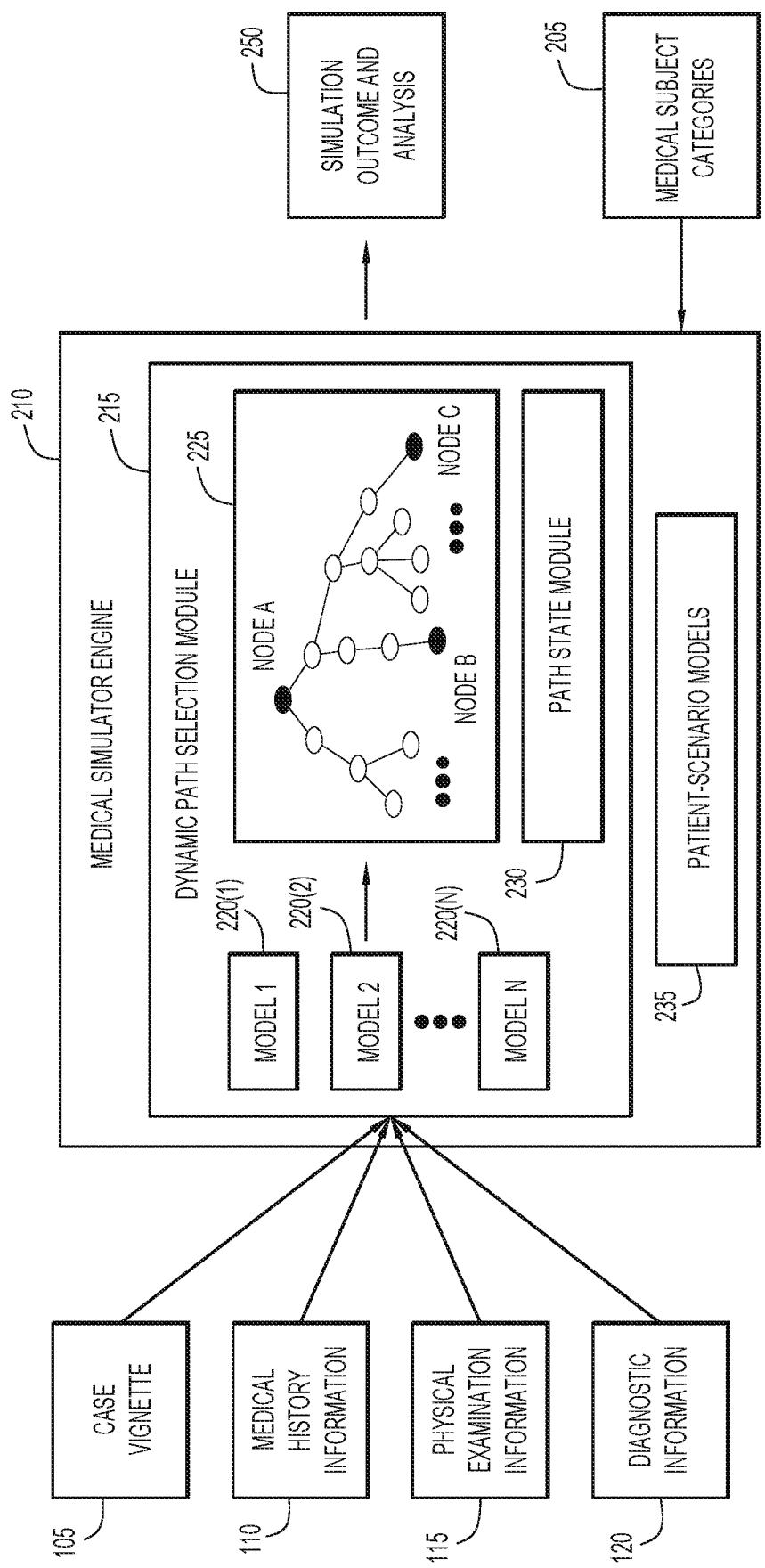
FIG. 2 is a block diagram of an example medical simulator engine, according to embodiments provided herein.

FIG. 2 is a block diagram of an example medical simulator engine 210, according to embodiments provided herein. In some aspects, the medical simulator engine presents various patient-scenario models 235 associated with a medical subject category 205 to a user. A case vignette 105 of the virtual patient may be presented to the user, wherein the case vignette is associated with a medical subject category and one or more patient-scenario models. The case vignette may describe, at a high level, the initial presentation and symptoms of the virtual patient. Based on the case vignette the user may interact with the virtual patient simulator to obtain additional medical history information 110, physical examination information 115, and diagnostic information 120 about the virtual patient.

Any suitable medical subject category in any discipline of medicine may be simulated, including neurological, respiratory, gastrointestinal, cardiovascular, reproductive, digestive, musculo-skeletal, endocrinological, infectious disease, surgery, anesthesiology, psychiatry, etc. For example, if the virtual patient presents with chest pain, then a cardiovascular model may be loaded in the simulator. If the virtual patient presents with abdominal pain, a gastrointestinal model may be loaded. In some cases, a patient may present with symptoms appearing in one subject category but the cause of the symptoms is in another subject category. Therefore, in some aspects, the cardiovascular model may be linked to gastrointestinal or other models, such that if the user completes the cardiac assessment correctly, the simulation may progress to another model in order to reach a diagnosis. In some aspects, in which multiple models may be relevant to the case vignette the system may load the models in order of priority, with priority determined by a risk of patient demise. In other aspects, the user may be presented with multiple models, and may select the appropriate model. In this example, model 1 220(1) may correspond to a cardiovascular model, while model 2 220(2) may correspond to a neurological model, while model N 220(N) may correspond to yet another model.

Each model may be associated with a plurality of pathways, which diverge at various decision points. Model 225 shows an example model with a plurality of pathways/branches. A dynamic path selection module 215 may govern progression through a model, such as model 225. Dynamic path selection module 215 determines which clinical patient history or portions thereof have been previously presented to a user, so that the same clinical patient history pathway will not be presented to a user during a subsequent simulation of the same model. Thus, the medical simulator engine, based on previous inputs from a user, adapts the simulation to that user. For example, different patient history scenarios and clinical patient history pathways may be presented to different users based on their respective inputs at the beginning of and during the simulation.

Path state module 230 may track which aspects of the simulation that a user has previously interacted with to ensure that the user does not traverse the same path or decision tree more than once if there is a good outcome with one management, e.g., non operative management of GI bleeding. The subsequent pathway may require operative management to save the patient. These scenarios would be presented to advanced level students/residents. In some cases, the path state module 230 may identify and flag decision tree pathways that have already been traversed, in order to hide these pathways from the user if a repetitive poor decision making pattern is detected to help with the user learning process. In some aspects, portions of a pathway that have previously been presented may be included, provided that the pathway from beginning to end is not entirely the same as the pathway that was presented to the user.

In this example, the simulation may begin at node A and may progress to another node, such as node B, which corresponds to either successful treatment or demise of the virtual patient. If the simulation is restarted, the simulation may again begin at node A, and will progress based on the decision making of the user along the management pathway. The simulation may progress through a pathway that, in its entirety, has previously been presented to a user again based on the decisions previously made. This tests the user's ability to learn from prior mistakes and adapt or face the same catastrophic outcomes.

In some aspects, when the user traverses a pathway that leads to successful treatment of the virtual patient, the simulation of the model may end. In other aspects, when the user traverses a pathway that leads to unsuccessful treatment of the virtual patient, the simulation of the model may proceed to node A, rendering the correct pathway to now be inaccessible, leading to patient deterioration despite attempts to return to the correct medical decision pathway and direct the user to an alternate correct management pathway, but still having a risk to make wrong decisions resulting in a catastrophic outcome.

In some aspects, the virtual patient simulator may comprise patient models that use decision trees. For example, a user is presented with a case vignette, and begins providing input, which accesses a portion of the decision tree. Subsequent inputs will move the user along a path of the decision tree. The dynamic path selection module, and in particular, the path state module 230, may monitor which portions of a decision tree that an individual user has traversed, so that the virtual patient simulator does not repeat portions of the decision tree already presented to the user, giving the user opportunities to traverse alternative but correct management protocols. Because the user is presented with different portions of the decision tree during a simulation, the user will not be able to memorize answers. Thus, the user interacts with the medical simulator (e.g., answers questions and performs actions) based on an understanding of medical knowledge and not based on memory of earlier portions of the simulation.

The user provides inputs to traverse through the nodes of pathways. If a correct decision is made, then the simulation proceeds normally. If an incorrect medical decision or oversight is made, the simulation may progress to a catastrophic sequence. In some scenarios, the user may exit the catastrophic sequence by making a series of subsequent correct decisions. In other cases, once a catastrophic sequence is initiated, the sequence is not reversible—instead, the simulation may proceed with the state of the patient continuing to deteriorate as a result of the missed diagnosis or wrong medical decision. A point scoring system will allow users to assess their performance even if the patient survives. They may score 70% even though the patient survives. This stimulates the users to read and perfect their management protocols, learning from the mistakes they made.

In other aspects, while obtaining additional information from modules 54, 52, and 56 regarding the patient of the case vignette, the condition of the patient will remain stable. However, in cases in which the condition of the patient deteriorates, the user may begin treatment and other interventions to stabilize the patient, even if the process of obtaining additional information is not yet complete to simulate real life patient management.

Information obtained by the user may be provided as input to the medical simulator engine 210, the information including medical history information 110, physical examination information 115, and diagnostic information 120. Aspects of the simulation may be driven by the information obtained by the user. For example, the user may provide input to the medical simulator engine 210 regarding which diagnostic tests and laboratory tests have been ordered. As the simulation progresses, in some aspects, the user may order additional tests, e.g., when a previous diagnostic test is inconclusive another test may be ordered, or the user may select a surgical option and/or a medical treatment option, e.g., administration of a therapeutic. While this interactive, adaptive process is occurring, the virtual simulator may simulate changing conditions of the patient (e.g., the patient condition may change slowly or quickly depending upon the medical condition, the input from the user to traverse nodes of a decision-based pathway, and the patient-scenario model). For example, if the user interprets the diagnostic test results incorrectly, administers a therapy that is contraindicated for the patient or condition, omits a key diagnostic test to determine a diagnosis of the patient, or reaches an incorrect medical decision, the simulator may enter a pathway which progresses to patient demise. On the other hand, if the user interacts with the system according to standard protocols, the condition of the patient may remain stable or progress along a pathway leading to patient deterioration at a slower rate, allowing sufficient time for the user to assess and manage the condition of the virtual patient. This will affect the scoring system at the conclusion of the scenario.

To pass the simulation, the user needs to avoid unfavorable patient outcomes (e.g., arising from medical or other errors). In some cases, the user may pass the simulation, even under circumstances of virtual patient demise provided that a medical management was appropriate but the virtual patient was too sick to save.

If the user does not pass the simulation, the user may restart the simulation. However, while the medical simulator engine presents the same medical subject category, a different patient-scenario model will be presented so that the user cannot memorize a particular patient-scenario model. Thus, the simulator evaluates medical working knowledge and an understanding of the subject being assessed. The simulation may be repeated multiple times until the user achieves an accurate diagnosis and treatment plan or level of acceptable proficiency.

Patient-scenario models 235 include various decision trees and/or flowcharts corresponding to a medical condition of a virtual patient. The patient-scenario model may be associated with a case vignette. A model may comprise a plurality of pathways in which each model comprises at least one favorable outcome and one or more unfavorable outcomes. The model may also comprise one or more catastrophic sequences. In general, a plurality of patient-scenario models may be associated with a medical subject category 205.

In some aspects, a virtual platform may be provided, allowing a user to treat patients virtually through either a CPR/ACLS protocol scenario with the virtual patient simulator providing feedback on each intervention performed. The CPR/ACLS protocol scenario may indicate whether the user achieves a good outcome or a poor outcome based on the user's interaction.

In some cases, the user may be able to perform virtual procedures on the patient during the course of the simulation. For example, a user may virtually perform endoscopic procedures related to the patient-scenario model, including but not limited to: colonoscopies, bronchoscopies or EGD techniques; common laparoscopies, DaVinci procedures; line placements, anoscopy, and rectal tube placement, etc. In some cases, virtual procedures may be available to advanced users after completing other medical subject categories and having practical experience (e.g., interns and/or residents).

Figure 3:
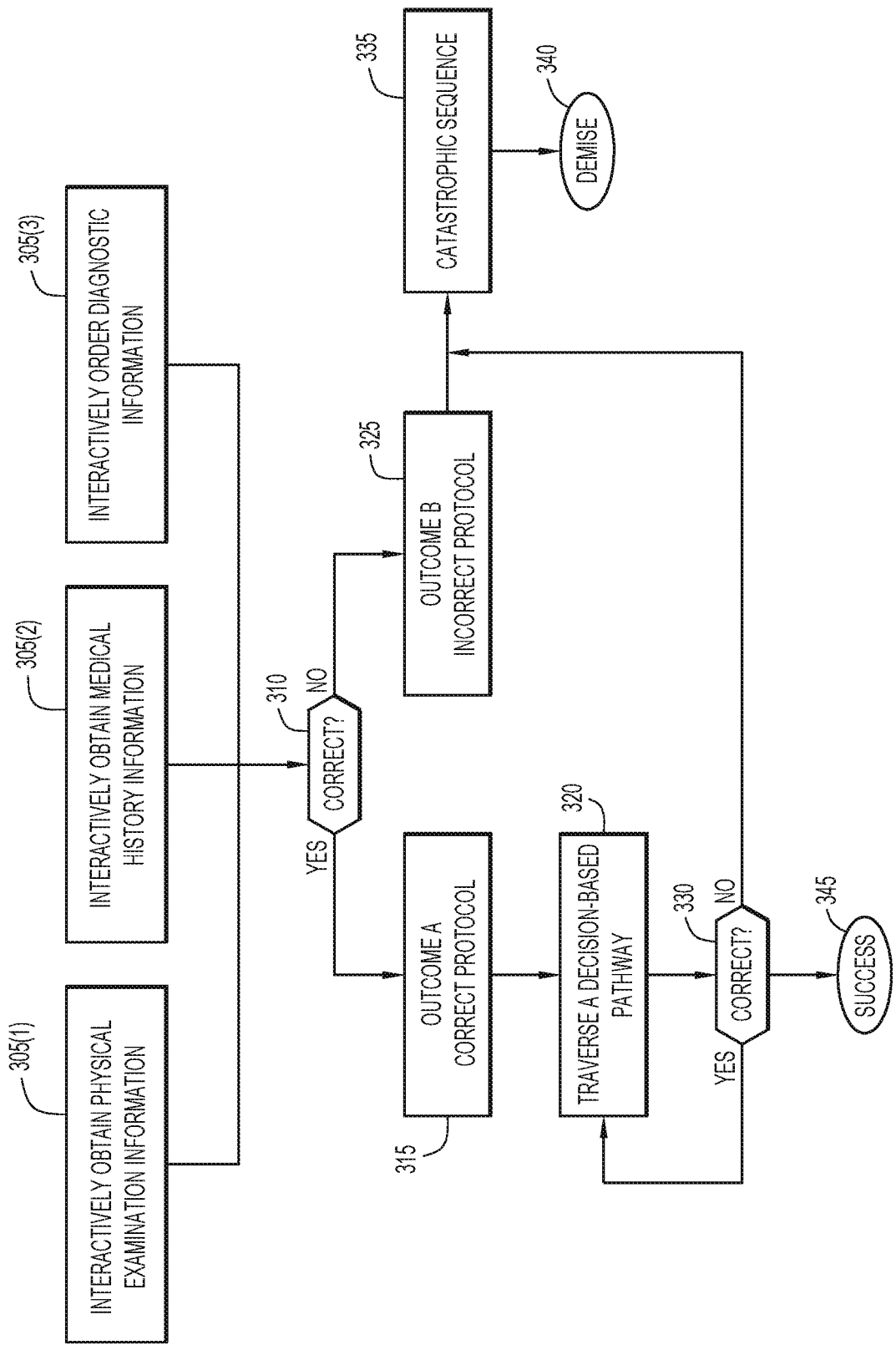
FIG. 3 is a flowchart illustrating general aspects of catastrophic sequences of the virtual patient system, according to embodiments provided herein.

FIG. 3 shows a flowchart of triggering a catastrophic sequence. In this flowchart, a user interacts with the virtual patient simulator to obtain various types of additional information at operations 305(1)-305(3). The virtual patient simulator determines at operation 310 whether the user has adhered to established medical protocols and/or procedures. At operation 315, the virtual patient simulator determines that the correct protocol has been followed, and the system begins progressing through a normal sequence 320 of simulation events, namely traversing a decision-based pathway, without a catastrophic sequence. At operation 325, the virtual patient simulator determines that an incorrect protocol has been followed or a wrong medical decision has been made, and the system progresses through a catastrophic sequence of simulation events at operation 335. The catastrophic sequence may be triggered immediately (not shown) or after progressing through one or more other decision nodes (as shown by the arrows). Incorrect protocols may include but are not limited to obtaining an incomplete medical history or failing to obtain a medical history, skipping aspects of the physical examination or omitting the physical examination altogether, failing to order laboratory tests or misinterpreting the laboratory results, failing to order diagnostic tests or misinterpreting the results, etc. If during a normal sequence of events, the user deviates from established medical protocols, as shown at operation 330, the user may also enter a corresponding catastrophic sequence. Once a catastrophic sequence is initiated, the simulation may continue to progress, allowing the user to continue to interact with the simulation. However, in some cases, regardless of whether the user performs standard medical protocols for the remaining part of the simulation, the demise 340 of the virtual patient may continue when a catastrophic sequence has been triggered. This provides a realistic simulation approach. Instead of being alerted at the time the wrong medical decision is made, the decision is allowed to continue and propagate patient deterioration through the simulation. In some aspects, the user may be able to view the simulation from start to finish, retrospectively, to identify the point at which the catastrophic sequence was initiated. Otherwise, if the user adheres to established medical protocols, the simulation may continue, through operations 320 and 330, until reaching a successful outcome at operation 345 (e.g., if there are no additional decision-based pathways and correct decisions have been made).

Figure 4:
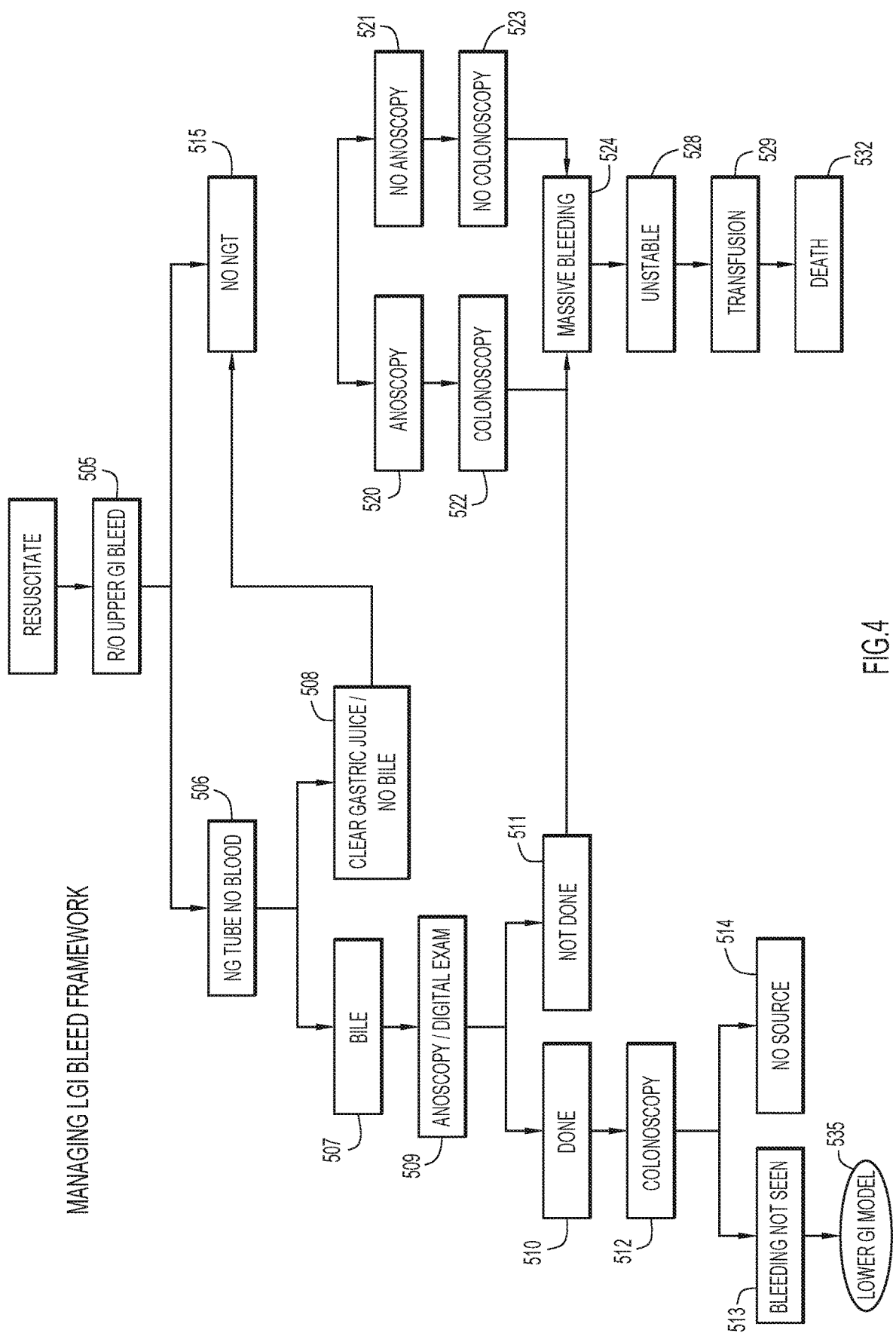
FIG. 4 is a flowchart illustrating a specific example of a catastrophic sequence of the virtual patient system, according to embodiments provided herein.

FIG. 4 shows an example flowchart for a gastrointestinal (GI) bleeding model including an example of how a catastrophic sequence may be triggered. The simulation loads a lower GI model to assess management of a GI bleed. Many different configurations are possible, and assessment and treatment of other medical conditions can be structured in a similar manner, such that failure to follow a standard medical protocol, or failure to correctly interpret information or making wrong medical decisions may have a downstream catastrophic effect on the virtual patient.

In particular, a wrong medical decision at operation 508 or progressing to operation 515 may trigger a catastrophic sequence, which leads to virtual patient demise at operation 532. On the other hand, following a correct procedure results in a different outcome, in which a diagnosis is made and/or the simulation progresses to another model (e.g., a lower GI model 535). A detailed discussion of the decision tree is provided below in the examples section.

In some aspects, the virtual patient may comprise or interface with a machine learning system that is configured to classify laboratory tests, diagnostic images, etc., into categories associated with a medical condition of the virtual patient. Any image classified by the machine learning system such as showing lung cancer may be provided to the user during the course of the simulation. If the user repeats this portion of the simulation, a different image may be provided to the user so that the user cannot rely on memory to interpret previously viewed images.

Similarly, a machine learning system may classify laboratory tests into a disease or non-disease category. If the user repeats an aspect of the simulation in which laboratory test results are provided, a different set of results indicative of the same disease may be provided to the user such that the user cannot rely on memory to interpret previously viewed laboratory results.

These concepts may also be extended to other types of medical information available in the simulation. For example, virtual patient medical histories and physical examination results may be classified into a respective disease category or a non-disease category. If the user repeats an aspect of the simulation in which medical history and/or physical examination information are provided, a different set of medical history and/or physical examination information indicative of the same disease may be provided to the user such that the user cannot rely on memory to interpret previously viewed information.

Thus, in an embodiment, the system may be provided with medical data sets (e.g., lab tests, images from radiology, physical examination, medical history), which are automatically classified by the machine learning system into respective disease categories, with minimal or no intervention by an administrator of the system. This approach allows new data to be provided to the simulator for the same disease category to ensure that the user relies on medical knowledge and not memorization during the simulation.

Figure 5:
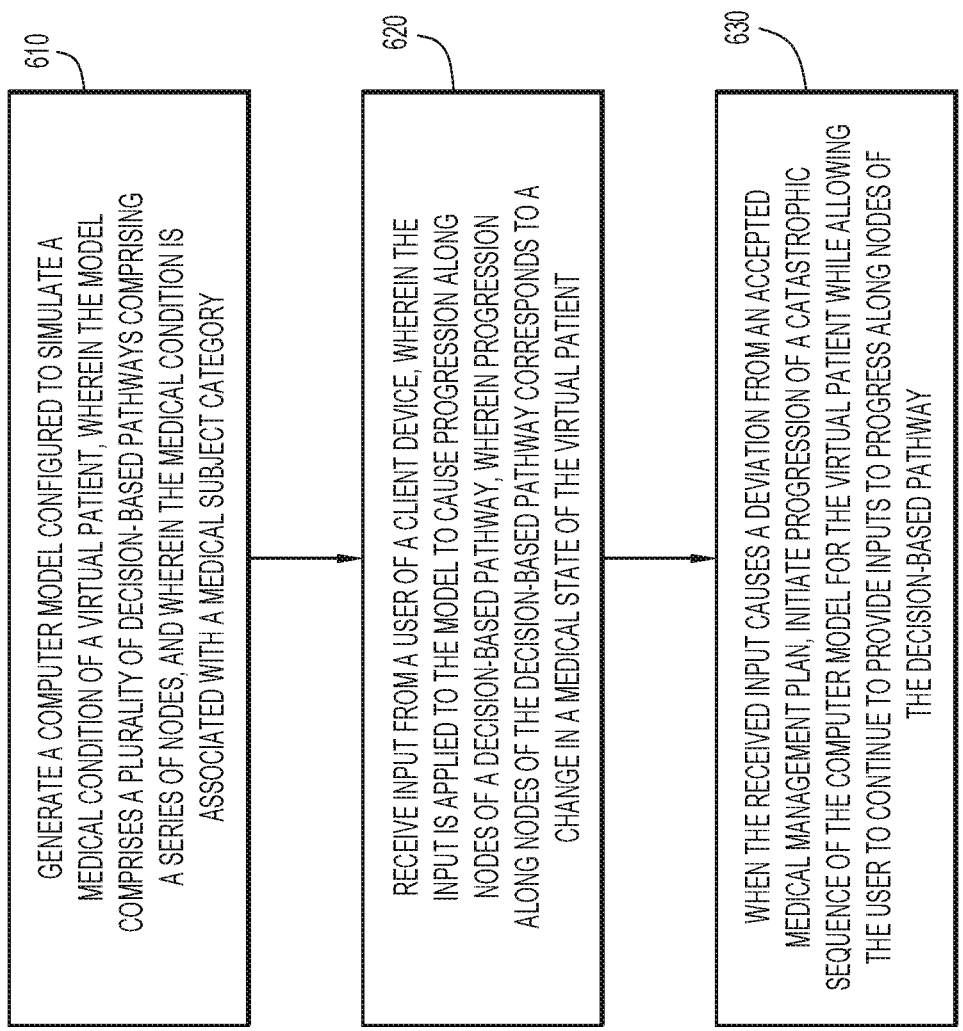
FIG. 5 is a flowchart showing exemplary operations at the server system, according to embodiments provided herein.

FIG. 5 is an operational flow chart comprising example operations according to the embodiments provided herein. At operation 610, a computer model configured to simulate a medical state of a virtual patient is generated, wherein the model comprises a plurality of decision-based pathways, and wherein the virtual patient is associated with a medical condition of a medical subject category. At operation 620, input is received from a user of a client device, wherein the input is applied to the model to cause progression along nodes of a decision-based pathway, wherein progression along the decision-based pathway corresponds to a change in a medical state of the virtual patient. At operation 630, when the received input causes progression along a decision-based pathway that is not in accordance with accepted medical standards, progression of a catastrophic sequence of the model for the virtual patient is initiated.

The embodiments provided herein are an improvement over current techniques, which may provide immediate feedback to a user when a wrong simulation decision is made thereby stopping the learning process. According to the presented techniques, the simulation is allowed to proceed, even when a wrong medical decision or oversight is made, to more realistically simulate a clinical setting. In such cases, the user may continue to treat and interact with the virtual patient. However, because a medical condition or critical information has been missed, the simulation allows the medical condition to worsen, and may lead to the demise of the virtual patient. Accordingly, these techniques allow users to work through complex interrelated medical scenarios. As the simulator is configured to vary decision-based pathways presented to a user, a user cannot rely on human memory to pass the simulation, but instead, needs to and has to rely on medical knowledge. Successful completion of a first model may progress to another model to diagnose a medical condition.

In some aspects, the embodiments provided herein may utilize machine learning techniques to perform object recognition associated with images and or text-based data. In such cases, a machine learning approach may be used to classify images and text-based data into categories associated with medical conditions, to provide a library of images and text-based data, which may be used as part of the virtual patient simulator.

Present techniques provide an improvement to the field of medical simulators. In particular, these techniques mimic emergency medical management situations, allowing medical conditions to progress as a function of time, even after incorrect medical decisions have been made. Unlike other simulators in which the simulation halts in response to a user error, present techniques allow the simulation to progress based on a timescale related to the medical condition. For example, if a patient is stable, and a minor error in a medical decision pathway is made, the condition of the patient may continue to deteriorate but in a slow manner. If a major error in a medical decision pathway is made, the condition of the patient may deteriorate rapidly. This approach mimics real-life conditions experienced in an emergency care setting, and helps practitioners improve their medical decision making under simulated duress. Additionally, the present techniques rely on a computing device and virtual patient simulator engine to perform the simulation. Thus, these techniques are inherently tied to functioning of a computing device. Accordingly, the present subject matter is integrated into virtual patient simulator and other types of simulation applications.

The above embodiments are not limited to the specific tasks or algorithms described above, but may include any process for simulating models comprising a plurality of decision-based pathways, in which some pathways are accepted protocol and other pathways are not. This approach can be used to generally train individuals to handle complex tasks in a realistic virtual setting.

The computer readable program instructions may be executed on a computer or other computing devices to cause a series of operational steps to be performed by the computer or other computing device, resulting in a computer implemented process that produces the desired result (e.g., simulation of the virtual patient based on models, etc.).

The software as presented herein (e.g., virtual patient simulator 50, etc.) may be provided on a non-transitory computer readable medium (e.g., CD-ROM, DVD floppy diskettes, magnetic and/or optical media, memory devices such as USB keys or external hard drives, etc.) for use with the systems (or stand-alone systems) as described herein.

A computer-readable medium may include any number of persistent storage devices (e.g., magnetic disk drives, solid state storage, etc.) and/or transient memory devices (e.g., RAM). Computer readable storage media include but are not limited to a portable compact disc read-only memory (CD-ROM), a portable computer diskette or floppy disk, a digital versatile disk (DVD), an erasable programmable read-only memory (EPROM or Flash memory), a hard disk, a memory stick, a random access memory (RAM), a read-only memory (ROM), a static random access memory (SRAM), etc., as well as any suitable combination of the foregoing. The computer readable code is stored on a non-transitory medium.

A computer readable program may be translated into instructions for performing operations according to the techniques set forth herein, including but not limited to: assembler instructions, configuration data for integrated circuitry, firmware instructions, instruction-set-architecture (ISA) instructions, machine instructions, machine dependent instructions, microcode, state-setting data, or either source code or object code written in any combination of one or more programming languages, including object oriented programming languages, and procedural programming languages, such as the "C" programming language or similar programming languages, languages for performing natural language processing, etc. Computer readable program code or instructions, stored on the computer-readable storage medium, is configured such that, when executed by a processor, the code or instructions causes the processing system to perform steps described above.

In other embodiments, the server or any one or more of the modules of server system 20 may be configured to perform the functions described above without the need for computer readable program code. For example, virtual patient simulator 50 (or any other suitable module) may comprise specialized hardware, such as one or more application-specific integrated circuits (ASICs). Hence, the features of the present invention described above may be implemented in hardware and/or software. For example, in some embodiments, the functional tiers described above may be implemented by executing computer instructions, by hardware independent of any computer instructions, or by any suitable combination of hardware and/or software.

The techniques presented herein may be applied to any desired type of computing environment (e.g., client-server, cloud-based computing, distributed computing, mainframe, network computing, stand-alone systems, etc.), and may be implemented by any number of any computing devices, including but not limited to desktops, servers, laptops, PDA, mobile devices, tablets, mainframes, etc.

The software corresponding to the techniques presented herein may be implemented in any suitable language, and may be developed by one of ordinary skill in the art, based upon the functional descriptions in the flowcharts and embodiments as set forth herein. Moreover, the software and/or algorithms as described herein are not limited to any particular order of operations, as set forth in the examples, but may include any order that accomplishes the functions as set forth herein. For example, two operations shown sequentially may, in fact, be executed substantially concurrently, or the operations may be executed in the reverse order, provided that the functionality for which the operations are designed is maintained.

While various embodiments and implementations of the present invention are described above and claimed, it should be understood that they have been presented by way of example only, and not limitation. For example, the virtual patient simulator is not limited to the specific models provided described herein. Many modifications and variations will be apparent to those of ordinary skill in the art without departing from the scope and spirit of the invention. The embodiments illustrated herein were chosen in order to best explain the principles of operation and of practical applications. Thus, the breadth and scope of the present invention should not be limited by any of the above-described exemplary embodiments.

Example 1. Obtaining Medical, Physical and Diagnostic Information

An example of the virtual patient simulator is provided herein. In this example, a virtual patient presents to the user with lower gastrointestinal (LGI) bleeding. The system provides a case vignette to the user, as a starting point for diagnosis and treatment of the virtual patient.

Virtual Case Vignette: A 65 year old with no prior history of bloody bowel movements presents to the ER with a two day history of having multiple painless bloody bowel movements, with dark red blood and no stool. Patient reports the following symptoms:
Dizziness
Mild nausea The user continues with obtaining a history of presenting illness and medical history of the patient by interacting with medical history module 54. Using this module, the user asks a series of questions to obtain the pertinent patient history from the simulator and then expounds the History of Presenting Illness to completion. The user then obtains a complete history by asking appropriate questions. Questions may include but are not limited to: (1) present medical conditions, e.g., hypertension (HTN), peripheral arterial disease, hypercholesterolemia, etc.; (2) current medications, e.g., amlodipine, lisinopril, simvastatin, baby aspirin, etc.; (3) past surgical history, e.g., open cholecystectomy, right femoral popliteal artery bypass, hysterectomy, right knee arthroplasty, right shoulder arthroscopy, etc.; and (4) allergies to medications, e.g., sulfa drugs, penicillin, etc.; (5) family history, e.g., hypertension, coronary artery disease, peripheral arterial disease, breast cancer, lung cancer, etc.; and (6) social history, e.g., former smoker, drinks alcohol occasionally, no use of drugs, etc. The user must then ask questions to complete the medical history module. For teaching and thoroughness purposes once the module is complete the user in some instances may not return to the Medical History module. The user must then ask questions to perform a complete Review of Systems (ROS).

The user may initiate the physical examination module 52, beginning with a clinical assessment. These questions may include: (1) assessing the general state of the virtual patient (e.g., alert or disoriented, acute distress or not distress, etc.); and (2) assessing vitals, including blood pressure (BP), heart rate (HR), respiration rate (RR), and oxygen saturation. For example, the system may provide the following parameters.

BP: 100/75
HR: 96
RR: 20
Saturation: 94%

The user also elicits information leading to and establishing a complete physical examination, including assessing Head, Ears, Eyes, Nose Throat (HEENT), Neck, Respiratory, Cardiovascular system (CVS), abdomen, rectal exam, Musculo Skeletal System (MSS), central nervous system (CNS), Genito-Urinal System (GUS), skin, and Breast etc. The system may then provide the following responses:

HEENT: Pale and moist mucosa and anicteric sclera
Neck: Soft and supple with no masses and no lymphadenopathy
Respiratory: Good inspiratory effort. Clear to auscultation bilaterally. No wheezing, no crackles, and no rales.
CVS: I and II HS heard with no added sounds. No gallops and no murmurs,
Regular rate and rhythm
Abdomen: Not distended. No bulges. Bowel sounds are mildly hyperactive. Non-tender and no masses on palpation. Resonant note on percussion.
Rectal Exam: Bloody stool, no hemorrhoids or rectal masses
MSS: Decreased distal pulses in bilateral lower extremities. No edema
CNS: No weakness, no deficits
Skin: No lesions, intact Examination findings for specific organ systems may not be provided to the user. The system tests the user's clinical knowledge, hence the user has to ask specific pertinent questions to elicit responses from the module (i.e. Was there any blood on rectal examination and what color was it?).

The user may also initiate the diagnostic testing module 56 to order laboratory tests, imaging tests, or other medical tests. In the following example, blood work is ordered for the virtual patient, and the results are returned. For example, returned results may include blood tests:

CBC: WBC-10.5
H/H: 8/25
Platelets: 276
CMP: Na-139
K: 3.7
Cl: 97
CO2: 24
BUN: 38
Cr: 1.5
AST/ALT/ALP/Bili-Normal Protein: 5.9
Albumin: 3.6
PT/PTT: PT 19.5
INR: 1.3
PTT: 32

The system may not provide generic results but may wait for prompts from the user asking for specific labs to assess the user's knowledge as to why the user is requesting specific tests and that the tests are pertinent (i.e. What was the H and H? What is the PT/INR?).

Imaging tests may be ordered and may include an X-ray of the chest/abdomen. For example, these results may indicate a negative result, which indicate no abnormal findings. Images may depict pathologies the user has to diagnose assessing the user's radiological acumen.

X-ray of chest, abdomen and pelvis—Negative
CT Scan abdomen and pelvis—Shows series of diagnostic images for interpretation Example 2. Pathways in a Model Once the user has completed the initial assessment modules, which include medical history information, physical examination information, and diagnostic information, the user begins interacting with the virtual patient simulator management/treatment pathways. If the user fails to perform the initial assessment, the virtual patient simulator may initiate a catastrophic sequence in which the virtual patient undergoes progressive deterioration, e.g., continued bleeding and becoming hypotensive, with the virtual patient deteriorating as a function of time and user intervention. At this point, the simulation may provide the opportunity to resuscitate the patient. For example, the user may resuscitate the virtual patient with crystalloids, using one or more large bore IV's and altering the progression of the medical management protocol pathway. The response may be decreased but with continued blood loss, due to the user missing a key diagnostic component, which was essential for the management module. This would result in a patient complication versus catastrophic event.

If the virtual patient simulator indicates that the patient is unstable, the user may have the opportunity to virtually type and crossmatch the patient's blood, and virtually administer one or more units of PRBC's by transfusion until the patient is stabilized.

Once the patient is stabilized, the virtual patient simulator presents the user with a multi-path flowchart or decision tree corresponding to various treatment pathways for the virtual patient. The flowchart or decision tree comprises a plurality of decision points at which respective paths may diverge. Input from the user may determine which path is selected and the eventual patient outcome.

Example 3. Model Pathways

With reference to FIG. 5, a detailed description of example pathways are provided. The presence of upper GI bleed model is accessed at operation 505. In Pathway A at operation 506, a nasogastric tube (NGT) is placed. The simulation may proceed to operation 507 at which point bile is aspirated, indicating that interpretation of the significance of NGT placement is correct to exclude an upper GI bleed. Alternatively, at operation 508, clear gastric juice may be aspirated or no bile may be aspirated indicating an upper GI bleed has not been excluded.

At operation 509, a digital exam or anoscopy may be performed. At operation 510, the procedure is completed. Ano-rectal causes such as hemorrhoids may be identified and suture ligation performed. At operation 511, a digital examination or anoscopy is not performed leading to potential massive bleeding from an easily managed ano-rectal cause.

At operation 512, a colonoscopy may be performed. If the source of the bleeding is found, it may be controlled with endoscopic techniques. Otherwise, bleeding will continue if the source is not identified. At operation 513, bleeding is not seen. At operation 514, bleeding is seen but the source is not identified. In this case, a bleeding scan may be performed and/or surgery may be performed (not shown).

At operation 515, a different path is taken after failing to exclude an upper GI bleed. At operation 515, the NGT tube is not placed and equates to operation 508 where it is placed but a clear aspirate or no aspirate is obtained, indicating that the NGT test has not excluded an upper GI bleed. At operation 520, an anoscopy may be performed. At operation 522, a colonoscopy may be performed. (Operation 521 corresponds with no anoscopy, while operation 523 corresponds to no colonoscopy.) If a source of bleeding is seen, endoscopic techniques may be applied. If the bleeding is not controlled, the virtual patient continues to bleed. At operation 524, massive bleeding ensues, if the user fails to exclude an upper GI bleed or ano rectal bleeding source. This leads to an unstable virtual patient at operation 528. Although a transfusion is performed at operation 529, the condition of the patient continues to deteriorate, with the virtual patient's demise at operation 532. Other techniques may be performed, e.g., a bleeding scan or surgery, but are not shown here.

Thus, in this example, the user interacts with the virtual patient simulator, and the simulator evaluates whether the user performs appropriate actions, in this case placement of a nasogastric tube (NGT). If the user fails to perform the procedure, or orders an incorrect procedure, the system progresses with continued bleeding ending with a catastrophic sequence.

In yet other embodiments, the user may interact with the system to virtually perform placement of the NGT tube. In other aspects, the system may return a result from placement of the NGT tube. In other embodiments, the user may interact with the system to virtually perform a colonoscopy or other suitable procedures.

In this example, a lower GI Bleed flowchart/decision tree is provided, and the user may traverse a pathway of the flowchart or decision tree based upon inputs from the user. In some aspects, a decision tree may reference another decision tree, such that when the initial basic decision tree is complete, the simulation may continue to another aspect but more complicated decision tree, as shown at operation 535.

In general, a medical subject category or discipline may have any number of disease models, each with any number of respective pathways, each pathway comprising a plurality of nodes. According to aspects of present techniques, a particular individual patient scenario corresponding to a disease model will not be presented to the user more than once during simulation of the model. In some aspects, the user may enter a node at a top of a pathway, and may progress along a pathway until exiting the pathway or progressing to a more advanced pathway in the decision making process of the disease. For a repeat simulation, the user may enter a node at a top of a pathway, and may progress along a different pathway based on changes in the decision making process until exiting the pathway or progressing to the advanced aspect of the model. While subsequent patient scenarios will not be the same, the disease severity and progression may overlap creating essentially new decision making processes and giving the user the variability experienced in practicing medicine.

Example 3. Multiple Scenarios

Based on the decisions by the user during the simulation, different pathways are initiated by the user's inputs.

In a pathway, the NGT tube is correctly placed, and bile is aspirated. If blood is present in the bile, then the simulation progresses through treatment for an upper GI bleed. If blood is not present, then the simulation progresses through treatment for a lower GI bleed. In this scenario, the correct protocol has been followed with regard to management of an upper GI bleed. When correct medical management protocols are followed based on accepted accepted medical decisions and management protocols, the virtual patient may stabilize and be successfully treated and managed. For repeat scenarios, the pathway may become more complex, increasing the virtual patient's acuity and thereby assessing a higher level of medical knowledge and understanding by the user.

In another pathway, the NGT tube is placed and does not exclude an upper GI bleed, e.g., as evidenced by obtaining clear gastric juice fluid without bile. If the user does not recognize the significance of the test, e.g., by leaving the NGT or repeating it, and proceeds with lower GI assessment, then the virtual patient simulation may appear to progress normally, allowing the user to continue to make medical decisions and to perform medical treatment. However, as the simulation proceeds, the patient becomes unstable and vitals deteriorate from an undiagnosed upper GI bleed. The patient may initially appear to improve due to intervention such as fluid or blood resuscitation, however, the uncontrolled bleeding continues, which leads to deterioration of the virtual patient and eventual demise.

In still another pathway, the user fails to order NGT placement. The simulation begins and appears to progress normally. The patient initially appears stable, with normal vitals and laboratory results. However, as the simulation progresses, the presence of the virtual patient's undetected upper GI bleeding causes the virtual patient to become unstable, with deteriorating vitals and abnormal laboratory tests. Due to the deterioration of the virtual patient, options such as surgery and possibly other procedures may become risky to perform. While surgery or pharmaceutical treatment may lead to a temporary period of stabilization, as the underlying cause of the patient bleeding has not been identified, the virtual patient continues to deteriorate, and the end result is virtual patient demise.

Various scenarios are possible, and according to the simulation, wrong medical decisions made early in the medical simulation may lead to downstream patient demise. Unlike other simulations, in which the user may be notified immediately of the wrong medical decision, according to present techniques, the user may continue to perform medical treatment (e.g., surgical procedures, administration of medications, observations, procedures, etc.). Accordingly, the virtual patient simulator provides a realistic simulation of medical care techniques in a medical emergency setting. Failure to meet a standard early in the simulation may not be correctable, depending on the extent to which the patient condition has deteriorated.

What is claimed is:

1. A computer-implemented method of simulating medical management for a patient with a virtual simulator using a medical simulator engine comprising:
    generate a pre-determined accepted medical management plan for a medical condition of the patient based on an input from a user regarding the medical condition of the patient, wherein the medical condition is associated with a medical subject category;
    generate a computer model configured to simulate the medical condition of the patient, wherein the computer model is generated based on the pre-determined accepted medical management plan and comprises a plurality of decision-based pathways comprising a series of nodes, wherein at least two of the plurality of decision-based pathways includes different medical subject categories and are given priority based on a risk of the patient;

receiving an unguided input from the user of a client device;

causing a progression along the series of nodes of a decision-based pathway based on the unguided input applied to the computer model and the medical condition of the patient such that a speed of the progression along the series of nodes of the decision-based pathway depends on the medical condition, the computer model, and the unguided input; and when the unguided input causes a deviation from the pre-determined accepted medical management plan, initiating a progression of at least one catastrophic sequence of the computer model for the patient while allowing the user to continue to provide the unguided input to progress along the series of nodes of the decision-based pathway, wherein, when the unguided input is in accordance with the pre-determined accepted medical management plan, the speed of the progression along the series of nodes of the decision-based pathway is at a different rate than when the unguided input causes the deviation from the pre-determined accepted medical management plan, and wherein the different rate is based on a degree of the deviation from the pre-determined accepted medical management plan.

2. The computer-implemented method of claim 1, wherein the deviation from the pre-determined accepted medical management plan causes at least one downstream complication or demise of the patient without impacting adjacent nodes of the decision-based pathway traversed during a simulation.

3. The computer-implemented method of claim 1, wherein the decision-based pathway is traversed once during a simulation of the computer model.

4. The computer-implemented method of claim 1, wherein the plurality of decision-based pathways include a first decision pathway and a second decision pathway, which are different from one another based on variations in user decisions and which comprise overlapping nodes.

5. The computer-implemented method of claim 1, wherein the unguided input includes stopping the at least one catastrophic sequence based on the user discovering the deviation from the pre-determined accepted medical management plan.

6. The computer-implemented method of claim 1, further comprising:

tracking, by the medical simulator engine, previously traversed nodes; and disabling at least one pathway comprising the previously traversed nodes from being displayed more than once during a simulation by varying complexity and acuity of the medical condition.

7. The computer-implemented method of claim 1, wherein the input from the user includes unguided interaction with the patient comprising obtaining information from the patient, the information includes a medical history of the patient, a physical state of the patient, and diagnostic data, to determine the medical condition of the patient, and the unguided input relates to performing medical testing on the patient, and performing virtual procedures on the patient, throughout a course of a simulation.

8. The computer-implemented method of claim 7, further comprising:

determining one or more portions of a patient-scenario model presented to the user in one or more previous unsuccessful attempts of the simulation; and excluding the one or more portions of the patient-scenario model in a current simulation.

9. The computer-implemented method of claim 7, further comprising:

determining a score obtained by the user for the simulation based, at least in part, on the speed of the progression along the series of nodes of the decision-based pathway and the degree of the deviation from the pre-determined accepted medical management plan.

10. The computer-implemented method of claim 7, wherein the unguided input further comprises an explanation for requesting to perform the medical testing.

11. The computer-implemented method of claim 1, wherein generating the pre-determined accepted medical management plan includes:

obtaining the input from the user, the input is in an unguided form and requests diagnostic testing of the patient to determine the medical condition for generating the pre-determined accepted medical management plan.

12. A computer-based system for simulating medical management of a patient comprising a virtual simulator with a medical engine and at least one processor configured to:

generate a pre-determined accepted medical management plan for a medical condition of the patient based on an input from a user regarding the medical condition of the patient, wherein the medical condition is associated with a medical subject category;

generate a computer model configured to simulate the medical condition of the patient, wherein the computer model is generated based on the pre-determined accepted medical management plan and comprises a plurality of decision-based pathways comprising a series of nodes, wherein at least two of the plurality of decision-based pathways includes different medical subject categories and are given priority based on a risk of the patient;

receive an unguided input from the user of a client device, cause a progression along the series of nodes of a decision-based pathway based on the unguided input applied to the computer model and the medical condition of the patient such that speed of the progression along the series of nodes of the decision-based pathway depends on the medical condition, the computer model, and the unguided input; and when the unguided input causes a deviation from the pre-determined accepted medical management plan, initiate a progression of at least one catastrophic or complicated sequence of the computer model for the patient while allowing the user to continue to provide the unguided input to progress along the series of nodes of the decision-based pathway, wherein, when the unguided input is in accordance with the pre-determined accepted medical management plan, the speed of the progression along the series of nodes of the decision-based pathway is at a different rate than when the unguided input causes the deviation from the pre-determined accepted medical management plan, and wherein the different rate is based on a degree of the deviation from the pre-determined accepted medical management plan.

13. The computer-based system of claim 12, wherein the deviation from the pre-determined accepted medical management plan causes downstream complications or a demise of the patient.

14. The computer-based system of claim 12, wherein the decision-based pathway is traversed once during a simulation of the computer model.

15. The computer-based system of claim 12, wherein the plurality of decision-based pathways include at least a first decision pathway and a second decision pathway, which are different from one another based on variations in user decisions and which comprise overlapping nodes.

16. The computer-based system of claim 13, wherein the unguided input causes stopping the at least one catastrophic or complicated sequence based on the user discovering the deviation from the pre-determined accepted medical management plan.

17. The computer-based system of claim 13, wherein the medical simulator engine is further configured to:
   track previously traversed nodes; and
   disable at least one pathway comprising the previously traversed nodes from being displayed more than once during a simulation by varying complexity and acuity of the medical condition.

18. A computer program product for simulating medical management for a patient with a virtual simulator using a medical simulator engine, the computer program product comprising a computer readable storage medium having program instructions embodied therewith, the program instructions, executable by a computer, to cause the computer to:
   generate a pre-determined accepted medical management plan for a medical condition of the patient based on an input from a user regarding the medical condition of the patient, wherein the medical condition is associated with a medical subject category;
   generate a computer model configured to simulate the medical condition of the patient, wherein the computer model is generated based on the pre-determined accepted medical management plan and comprises a plurality of decision-based pathways comprising a series of nodes, wherein at least two of the plurality of decision-based pathways includes different medical subject categories and are given priority based on a risk of the patient;
   receive unguided input from the user of a client device,
   cause a progression along the series of nodes of a decision-based pathway based on the unguided input applied to the computer model and the medical condition of the patient such that a speed of the progression along the series of nodes of the decision-based pathway depends on the medical condition, the computer model, and the unguided input; and
   when the unguided input causes a deviation from the pre-determined accepted medical management plan, initiate a progression of at least one catastrophic sequence of the computer model for the patient while allowing the user to continue to provide the unguided input to progress along the series of nodes of the decision-based pathway,
   wherein, when the unguided input is in accordance with the pre-determined accepted medical management plan, the speed of the progression along the series of nodes of the decision-based pathway is at a different rate than when the unguided input causes the deviation from the pre-determined accepted medical management plan, and
   wherein the different rate is based on a degree of the deviation from the pre-determined accepted medical management plan.

19. The computer program product of claim 18, wherein the deviation from the pre-determined accepted medical management plan causes a downstream demise or complications of the patient.

20. The computer program product of claim 18, wherein the program instructions further cause the computer to:
   track, by the medical simulator engine, previously traversed nodes; and
   disable at least one pathway comprising the previously traversed nodes from being displayed more than once during a simulation by varying complexity and acuity of the medical condition.

* * * * *